US00PP10395P

United States Patent [19]

Trees

[11] Patent Number: Plant 10,395

[45] Date of Patent: May 12, 1998

[54] GERANIUM PLANT NAMED 'PURPLE ROSE'

[75] Inventor: Scott C. Trees, Arroyo Grande, Calif.

[73] Assignee: Ball Horticultural Company, West Chicago, Ill.

[21] Appl. No.: 697,258

[22] Filed: Aug. 21, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

| | | | |
|---|---|---|---|
| P.P. 7,083 | 12/1989 | Hofmann | Plt./87.12 |
| P.P. 8,524 | 12/1993 | Trees | Plt./87.12 |
| P.P. 9,970 | 7/1997 | Hofmann | Plt./87.12 |

OTHER PUBLICATIONS

GTITM UPOVROM Citation for 'Purple Rose' PBR 96–899, Jul. 5, 1996.

*Primary Examiner*—James R. Feyrer
*Assistant Examiner*—Kent L. Bell
*Attorney, Agent, or Firm*—Burns, Doane, Swecker & Mathis, L.L.P.

[57] ABSTRACT

The new and distinct *Pelargonium* × *hortorum* cultivar named 'Purple Rose' is provided. This new Zonal Geranium was the result of a controlled breeding program wherein a plant designated 6714-17 (non-patented in the United States) was pollinated by a plant designated 6707-13 (non-patented in the United States). The new cultivar forms attractive semi-double fuschia florets having an eye of orange and red. Medium green foliage with zonation is well retained during shipment. The growth habit is vigorous self-branching and does not require the use of a growth regulator.

1 Drawing Sheet

SUMMARY OF THE INVENTION

The present invention comprises a new and distinct Geranium cultivar, botanically known as *Pelargonium* × *hortorum* Bailey, and hereinafter is referred to by the cultivar name 'Purple Rose'.

The new cultivar is a product of a planned breeding program which had the objective of the creation of a Geranium cultivar that exhibits uniform flowers, medium green foliage, a vigorous self-branching growth habit that requires no growth regulator, a propensity for rapid rooting, and stable foliage coloration during shipment.

The breeding program that resulted in the production of the new cultivar of the present invention was carried out in a controlled environment during 1992 at Arroyo Grande, Calif., U.S.A. The female parent (i.e., seed parent) was a plant designated 6714-17 (non-patented in the United States) which exhibits semi-double dark cherry florets with dark green foliage. The male parent (i.e., pollen parent) was a plant designated 6707-13 (non-patented in the United States) which exhibits single purple florets with medium green foliage. The parentage of the new 'Purple Rose' cultivar can be summarized as follows:

6714-17 × 6707-13.

'Purple Rose' was discovered and selected during 1993 as a highly distinctive flowering plant from among the progeny of the stated cross at Arroyo Grande, Calif., U.S.A. This plant was initially designated BFP-1380.

It was found that the new cultivar of the present invention:

(a) exhibits attractive semi-double fuschia florets having an eye of orange and red,
(b) forms attractive medium green foliage with zonation, and
(c) exhibits a vigorous self-branching growth habit in the absence of a growth regulator.

After senescence the flowers abscise and drop. To date, observations of the new 'Purple Rose' cultivar have not demonstrated resistance to Botrytis or any other specific disease.

The first act of asexual reproduction of the 'Purple Rose' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of unique characteristics as herein described for the 'Purple Rose' cultivar is fixed and is retained through successive generations of such asexual reproduction.

The new 'Purple Rose' cultivar has not been observed under all possible environmental conditions. Accordingly, the described phenotype may vary somewhat with variations in the environment, such as temperature, light intensity, and day length.

Of the many commercial cultivars, the 'Fox' cultivar (U.S. Plant Pat. No. 7,083) is considered to be the most similar to the new cultivar of the present invention. When the new cultivar of the present invention is compared to the 'Fox' cultivar, it is found that the new 'Purple Rose' cultivar exhibits a more vigorous growth habit (e.g., a height of approximately 24 to 25 cm. vs. approximately 19 to 22 cm.), smaller umbels (e.g. approximately 8 to 10 cm. × approximately 5 to 6 cm. vs. approximately 9 to 11 cm. × 6 to 8 cm.), and smaller florets (e.g., a diameter of approximately 4.3 to 4.7 cm. vs. 4.8 to 5.1 cm.).

The new cultivar of the present invention is being marketed, Inc. under the Designer trademark.

BRIEF DESCRIPTION OF THE PHOTOGRAPH

The accompanying photograph shows the new 'Purple Rose' cultivar with colors being as nearly true as it is reasonably possible to make the same in a color illustration of this character. The plant was being grown in a greenhouse at West Chicago, Ill., U.S.A. The appearance of a typical overall plant including the flower and foliage is illustrated.

DETAILED DESCRIPTION

The following observations, measurements and comparisons describe plants grown in greenhouses located at West Chicago, Ill., U.S.A., under conditions which approximate those generally used in commercial practice. In the following description, color references are made to The R.H.S. Colour Chart of The Royal Horticultural Society, London, England. The color values were determined on September 9th, under natural light conditions of 200 footcandles.

Classification:

*Botanical.*—*Pelargonium* × *hortorum* Bailey, cv. 'Purple Rose'.

*Commercial.*—Zonal Geranium.

Inflorescence

A. Umbel:

*Average diameter.*—Approximately 8 to 10 cm. compared to approximately 9 to 11 cm. for the 'Fox' cultivar.

*Average depth.*—Approximately 5 to 6 cm. compared to approximately 6 to 8 cm. for the 'Fox' cultivar.

*Peduncle Length.*—Approximately 14 to 17 cm. compared to approximately 13.5 to 17 cm. for the 'Fox' cultivar.

*Pedicel length.*—Approximately 3 to 3.6 cm. compared to approximately 3 to 3.5 cm. for the 'Fox' cultivar.

*Number of umbels/plant.*—When grown in a 10 cm. pot at 9 weeks after the sticking of a rooted cutting, there commonly are approximately 3 to 4 umbels per plant.

The 'Fox' cultivar also commonly forms approximately 3 to 5 umbels per plant.

*Number of florets/umbel.*—When grown in 10 cm. pots at 9 weeks, approximately 22 to 27 florets per umbel commonly are formed. This compares to approximately 21 to 34 florets per umbel for the 'Fox' cultivar under the same growing conditions.

*Buds.*—Elliptical in configuration, initially Red Group 52A and changing to Red-Purple Group 57A at the time of opening, and approximately 10 to 11 mm. in length and approximately 5.7 to 6.3 mm. in width. The buds commonly point downward when first formed, and then tend to assume an upright posture as they open.

*Pedicels.*—Commonly approximately 2.4 to 3.3 cm. in length. This compares to length of approximately 3.8 to 5.2 cm. for the 'Fox' cultivar.

B. Corolla:

*Average diameter.*—Approximately 4.3 to 4.7 cm. compared to approximately 4.8 to 5.1 cm. for the 'Fox' cultivar.

*Form.*—Both the 'Purple Rose' cultivar and the 'Fox' cultivar are semi-double with at least one petaloid.

*Petals.*—Spatulate shaped, dull in appearance, and smooth. Commonly approximately 5 to 6 petals are present per floret. This compares to approximately 7 to 12 petals per floret for the 'Fox' cultivar.

*Number of petaloids.*—Commonly forms approximately 1 petaloid per floret whereas the 'Fox' cultivar commonly forms 5 to 9 petaloids per floret.

*Color.*—General tonality from a distance of three meters: Bright purple. The petal coloration tends to fade somewhat with age. Adaxial: Red-Purple Group 66A at the outer two-thirds with the proximal one-third of the petals commonly being Red Group 43B. This can be compared to Red-Purple Group 66A with bases of Red Group 43A for the 'Fox' cultivar. Abaxial: A little darker than Red Group 55A at the distal edges and Red Group 52A at the base. This can be compared to Red-Purple Group 61C for the 'Fox' cultivar.

C. Reproductive organs:

*Androecium.*—The anthers are commonly approximately 2.2 mm. in length. The pollen color is Orange Group 26B. This can be compared to Orange Group 28B for the 'Fox' cultivar. The filaments are approximately 6 to 8 mm. in length.

*Gynoecium.*—The pistil length commonly is approximately 11 mm. There is a single stigma which commonly has a length of approximately 4 mm. which commonly branches into 5 parts, and the style length is approximately 5 mm.

*Fertility.*—Commonly does not produce fruits in the absence of mechanical fertilization.

D. Spring flowering response period: Approximately 6 to 7 weeks from rooted cuttings under greenhouse conditions.

E. Outdoor flower production: Freely flowering under outdoor growing conditions with substantially continuous blooming.

F. Durability: Ships well.

Plant A.

Foliage: Medium green with zonation. The leaf texture is pilose. The rib and vein pattern is palmate.

*Form.*—Reniform, with a cordate base.

*Margin.*—Bi-crenate.

*Color.*—Adaxial: Yellow-Green Group 146B at the center and a darker Yellow-Green Group 146A elsewhere for both the 'Purple Rose' cultivar and the 'Fox' cultivar. Abaxial: Yellow-Green Group 146B for both the 'Purple Rose' cultivar and the 'Fox' cultivar.

*Size.*—Approximately 8.5 cm. in width at the widest point and approximately 7.6 cm. in length. This compares to approximately 8.8 cm. in width at the widest point and approximately 7.5 cm. in length for the 'Fox' cultivar.

*Petioles.*—Commonly approximately 3.5 to 4.5 cm in length. This compares to a length of approximately 3.8 to 5.2 cm. for the 'Fox' cultivar.

General appearance and form:

*Internode length.*—Commonly varies from approximately 0.5 to 1 cm. for both the 'Purple Rose' cultivar and the 'Fox' cultivar.

*Branching pattern.*—Freely basal branching. No pinching is required to obtain self-branching. A vigorous self-branching growth habit is observed in the absence of a growth regulator.

*Height.*—Approximately 24 to 25 cm. above a 10 cm. pot at 9 weeks under standard greenhouse conditions. This compares to approximately 19 to 22 cm. for the 'Fox' cultivar.

I claim:

1. A new and distinct cultivar of Geranium plant named 'Purple Rose', substantially as herein shown and described, which:

(a) exhibits attractive semi-double fuschia florets having an eye of orange and red, (b) forms attractive medium green foliage with zonation, and (c) exhibits a vigorous self-branching growth habit in the absence of a growth regulator.

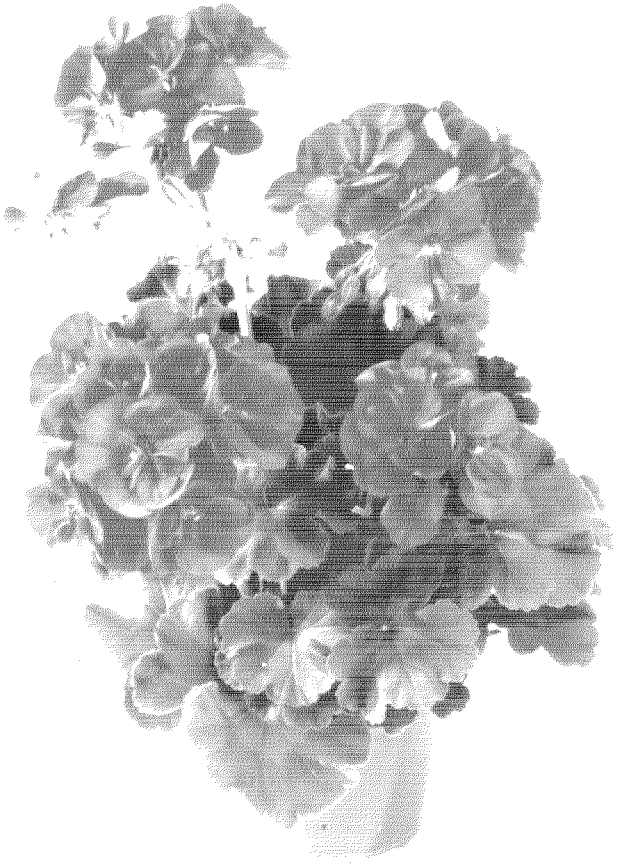

* * * * *